United States Patent [19]
Garvey, III et al.

[11] Patent Number: 5,817,928
[45] Date of Patent: Oct. 6, 1998

[54] METHOD AND APPARATUS FOR LUBRICATION FLUID ANALYSIS

[75] Inventors: Raymond E. Garvey, III, Loudon; Anthony Grahame Fogel; Anthony John Hayzen, both of Knoxville, all of Tenn.

[73] Assignee: CSI Technology, Inc., Wilmington, Del.

[21] Appl. No.: 838,009

[22] Filed: Apr. 14, 1997

[51] Int. Cl.⁶ .......................... G01N 03/56; G01N 33/30; G01R 27/26
[52] U.S. Cl. .............................. 73/53.05; 73/10; 324/698
[58] Field of Search .............................. 73/53.05, 53.01, 73/10; 324/698, 71.1, 204

[56] References Cited

U.S. PATENT DOCUMENTS

| | | | |
|---|---|---|---|
| 2,133,674 | 10/1938 | Stamback | 265/2 |
| 2,672,756 | 3/1954 | White | 73/215 |
| 3,025,698 | 3/1962 | Schultze et al. | 73/53 |
| 3,357,024 | 12/1967 | Mordecai | 346/1 |
| 3,526,127 | 9/1970 | Sarkis | 73/64 |
| 4,082,511 | 4/1978 | Bedford | 23/230 HC |
| 5,313,824 | 5/1994 | Herguth et al. | 73/53.05 |
| 5,452,695 | 9/1995 | Bedi | 123/196 A |
| 5,571,950 | 11/1996 | Waddoups et al. | 73/53.05 |
| 5,604,441 | 2/1997 | Freese et al. | 324/663 |
| 5,679,883 | 10/1997 | Wedeven | 73/10 |

*Primary Examiner*—Herzone E. Williams
*Assistant Examiner*—J. David Wiggins
*Attorney, Agent, or Firm*—Luedeka, Neely & Graham, P.C.

[57] ABSTRACT

A method is provided for evaluating a multiplicity of lubrication quality parameters. For a particular lubrication system, a parameter profile is designated to define all the measurable parameters to be monitored. Each parameter in the profile is assigned to single category respective to WEAR, CHEMISTRY and CONTAMINATION. Parameter values are proportionalized in a finite number of increments between acceptable and unacceptable limits. The worst case parameter of a category is selected to represent that category on a 3-axis, Cartesian graph for placing a data point along the respective category axis. Three data points respective to the three axes are linked with a triangular plane, the area of which is representative of the system quality state.

13 Claims, 5 Drawing Sheets

Fig. 1

| ISO 4406 CHART | | |
|---|---|---|
| RANGE NUMBER | NUMBER OF PARTICLES PER ml | |
| | MORE THAN | UP TO AND INCLUDING |
| 24 | 80,000 | 160,000 |
| 23 | 40,000 | 80,000 |
| 22 | 20,000 | 40,000 |
| 21 | 10,000 | 20,000 |
| 20 | 5,000 | 10,000 |
| 19 | 2,500 | 5,000 |
| 18 | 1,300 | 2,500 |
| 17 | 640 | 1,300 |
| 16 | 320 | 640 |
| 15 | 160 | 320 |
| 14 | 80 | 160 |
| 13 | 40 | 80 |
| 12 | 20 | 40 |
| 11 | 10 | 20 |
| 10 | 5 | 10 |
| 9 | 2.5 | 5 |
| 8 | 1.3 | 2.5 |
| 7 | .64 | 1.3 |
| 6 | .32 | .64 |

METHOD AND APPARATUS FOR LUBRICATION FLUID ANALYSIS

FIELD OF INVENTION

This invention relates to methods of and instruments for evaluating the quality of a lubrication or power transmission fluid and/or the deterioration status of a machine the fluid serves.

BACKGROUND OF THE INVENTION

Owners and operators of engines and industrial machinery have long known that good lubrication of relatively sliding or rolling machine elements was essential to long machine life and reliability. It is also long been known that certain characteristics of a lubrication or power transmission fluid are indicative of the machine wear status or state of deterioration.

However, many if not most of such characteristics are simply operational givens for certain machines and applications. For example, water in the lubrication system of a steam turbine main bearing may be disastrous due to the heavy loads carried at high speeds. However, considerable water may be tolerated by the lubrication system of a sea vessel propeller shaft thrust bearing due to the machine design, lubricant formulation and relatively slow speed: notwithstanding heavy loading.

In another example, the accumulation of water, soot and acid in the lubrication system of an intermittently operated, internal combustion engine is essentially unavoidable. These contaminants are products of the combustion process. Unavoidable blow-by from the combustion chambers allow direct contact between combustion products and the lubrication fluids. When the engine is stopped, the gaseous combustion products cool, condense and mix directly with the lubricants.

In some cases a lubrication fluid contaminant such as moderate quantities of soot that may be present in isolation from other contaminants, may be relatively harmless to the lubrication system. Although excessive quantities of soot can foul piston rings or plug oil drain channels, moderate quantities of soot may be circulated with the lubrication fluid inconsequentially.

A myriad of tests, both chemical and physical, are known for testing one or more lubrication oil characteristics. The results of such tests are frequently reported in a scramble of physical units: English and metric, less ratios and indices. Considerable training is required to simply evaluate the relevance of many test results to a particular machine or system. More significantly, considerable understanding of a particular machine or system is frequently required to even specify those tests having relevance to the machine or system to be evaluated. For example, responsible maintenance of a power transmission gearbox requires the technician to monitor mechanical wear, oil oxidation, acid buildup, the presence of water and other contaminants and the depletion of anti-wear, anti-oxidant and anti-scuff oil additives such as zinc, silicon and chromium. Surveillance of these properties requires the results of a test battery characterized as a "profile".

A "profile" is a collection of tests appropriate to a specific mechanical system. For example, a transmission or gearbox test profile may include (a) wear debris analysis (b) viscosity test (c) spectro metals (wear, additives, contaminants) test (d) fourier transform infrared (FTIR) spectroscopy (e) total acid number (TAN) and (f) water.

Comparatively, surveillance of a hydraulic power system should include (a) a particle count of solid contaminants, a measure of anti-wear additive depletion, a measure of water entrainment, a measure of oil oxidation, a measure of acid development and a measure of component wear. The test profile for such a hydraulic system would therefore include: (a) a particle count; (b) a viscosity measurement; (c) a spectro metals test; (d) an FTIR spectroscopy test; (e) a total acid number; and, (f) a water test.

A viscosity measurement windows the physical stability of an oil sample. A change in viscosity presages leakage, loss of pressure, loss of control precision and accelerated wear. Usually, viscosity is a relatively constant value until affected by changes in temperature, pressure, contamination and/or mechanical agitation. Contamination influences include particulates, water, air, fuel and chemicals.

Generally considered, a 20% increase or a 10% decrease in viscosity suggests the need for an oil change or other corrective action. Although viscosity is usually a stable characteristic, it may become volatile in the presence of contaminants. Dimensional units of viscosity are represented by the "poise", given in (gm mass)/(sec)(cm) or dynes)(sec)/(cm$^2$). Other dimensional systems include the "stoke" in cm$^2$/sec, the saybolt in seconds at 130° F. or the Engler in degrees. Typically, machine lubrication oil viscosity may span from 42 to 400 centipoise at 60° F.

Chemical instability of a lubricant is the consequence of heat, mechanical stress and contamination. Oxidation of oil leads to increased viscosity, increased acidity and the formation of degradation products such as gum, slime, varnish and sludge.

Chemical stability of a lubrication oil is evaluated by a neutralization number, a total acid number (TAN) or a total base number (TBN). A fresh lubricant or hydraulic oil is alkaline. Oxidation increases the acidity. Chemical stability does not usually change rapidly and any change in the neutralization number is an indication that oil degradation is beginning to occur and that oil life is diminishing. The units of neutralization numbers are mg KOH per gram of oil.

Additives are used in an industrial lubricant to enhance a property or add a new property. Predominantly, additives are used to neutralize the consequences of heat, contamination and moisture. Commonly blended additives include anti-wear additives, anti-oxidants, corrosion inhibitors and viscosity index modifiers.

Additive levels are measured with spectrographic oil analysis or Fourier transform infrared analysis (FTIR). By quantifying the presence of basic elements in an oil, an estimate of the useful life or availability of the additive may be proposed. Physical units related to such measurements may be traditional units of concentration or density.

Particle contamination of a machine lubrication system is a significant root cause of machine wear and component failure. The presence of particles in a system tends to generate more particles exponentially. Fortunately, numerous methods, mechanisms and strategies are available to control particle concentration and contamination i.e. filter media, adsorption beds and fluid replacement or replenishment. Generally, a balance is established between the number of particles entering a system and the number which are removed. The level and stability of that balance has a direct bearing on machine life.

Figure 1:
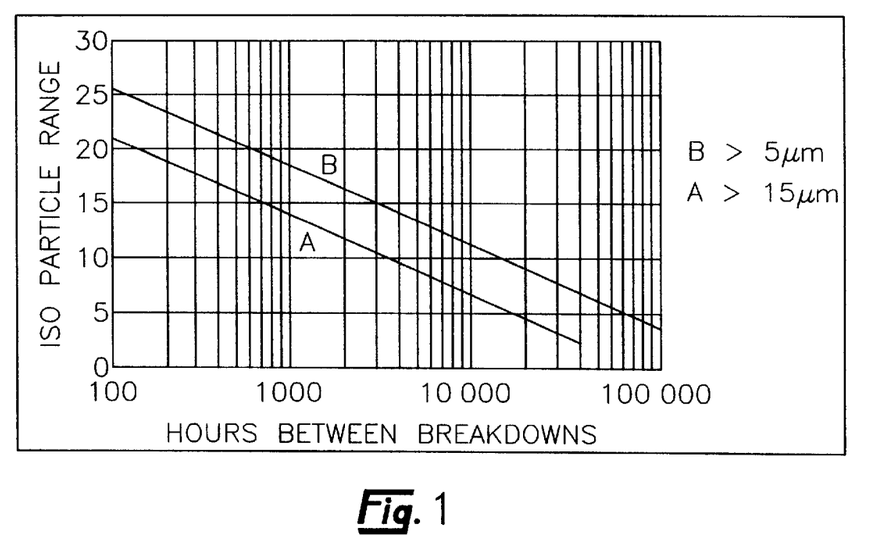
FIG. 1 is an ISO machine performance graph.
Figure 2:
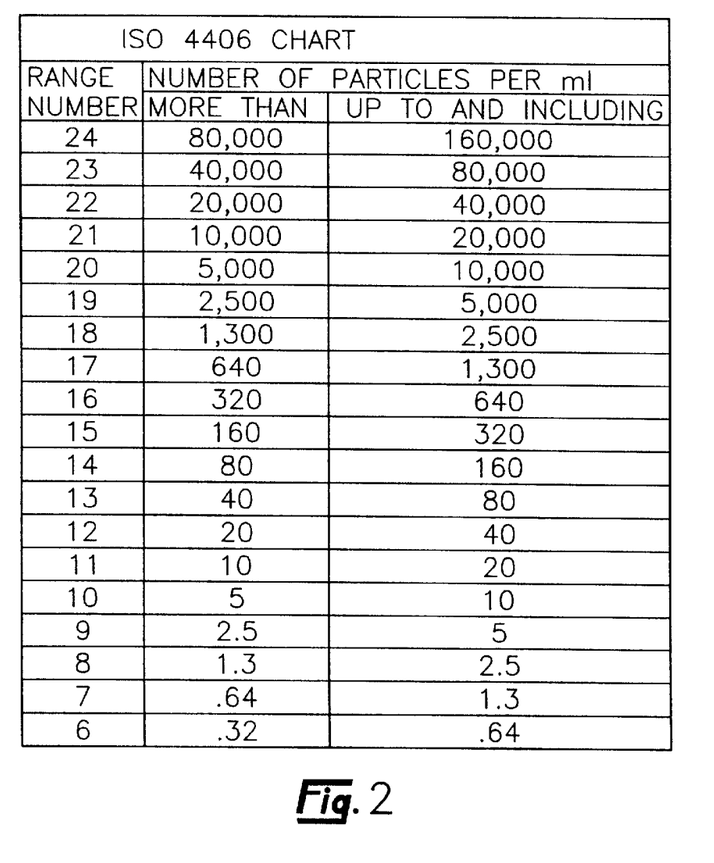
FIG. 2 is an ISO machine performance chart.

With respect to the chart of FIG. 2, by ISO standard 4406, the International Standards Organization (ISO) has established a system of particle concentration increments for fluid systems, each increment being uniquely identified by a range number. These ISO 4406 increment identification values are the ordinate unit scale for FIG. 1. Plotted exponentially along the FIG. 1 abscissa are operating hours between terminal breakdowns for a particular pump application. The "A" line of FIG. 1 charts the operating consequence of a particle size: spectrum that includes particles 15 µm and less. The "B" line of FIG. 1 charts the operating consequence of a particle size spectrum that includes particles of 5 µm and less.

It may be determined from FIGS. 1 and 2 that a pump in this application may be expected to operate about 14,000 hours if the lubrication system is filtered to remove particles having a diameter greater than 5 µm (FIG. 1, line B) and the filter system is effective to keep the particulate concentration between 5 and 10 particles per ml of lubrication fluid (ISO 4406, Range 10). Comparatively, if the particle concentration in the system is allowed to accumulate to between 160 and 320 particles per ml (ISO 4406, Range 15), notwithstanding maintenance of the small, 5 µm and less, particle size, the expected pump life is reduced to only 3000 hours; less than ¼ of a pump life expectancy when operated with a Range 10 particle concentration in the lubrication system.

Consider next, the impact of particle size. When the pump lubrication system is filtered to remove particles having a diameter greater than 15 µm (FIG. 1, line A) and maintained to keep the particle concentration between 5 and 10 particles per ml of oil (ISO 4406, Range 10), the pump life expectancy is 1200 hrs. When the particle concentration in that lubrication system grows to 160 to 320 particles per ml, (ISO 4406, Range 15) the pump life expectancy is reduced to 530 hours.

Particle counts in units of particles per unit of fluid volume may be obtained photometrically from a working system on a real time basis. More sophisticated instruments may further segregate the count into size groupings.

Moisture is another lubrication system contaminant that contributes to rapid oil degradation and machine failure. It may be present in the oil as free water, as an oil/water emulsion and in dissolved combination with hydroscopic additives. An oil contaminated with dissolved water may appear clear and clean. As moisture contamination levels increase to exceed the combination capacity of combined additives, the additional water begins to emulsify with the oil. When emulsification occurs, the oil will begin to appear cloudy or foggy.

Free moisture in an oil system occurs when the oil can no longer emulsify all of the water invading the system. Unlike particle, contamination, moisture is almost always ingested from the environment. The most obvious effects of moisture on a machine lubrication system and its components are rust and corrosion. Additionally, however, moisture reacts with long chain polymers to form stick substances which clog filters and valve openings. Since moisture vaporizes at a much higher pressure than lubrication and hydraulic oils, cavitation can occur when entrained moisture moves from a low pressure to higher pressure areas in a pump.

Roller element bearings are especially sensitive to moisture. In the elastohydrodynamic lubrication zones where a roller contacts the bearing race, momentary forces are in hundred of pounds per square-inch. Moisture contaminated oil compresses thereby allowing surface-to-surface contact under great force and causing excess wear.

Figure 3:
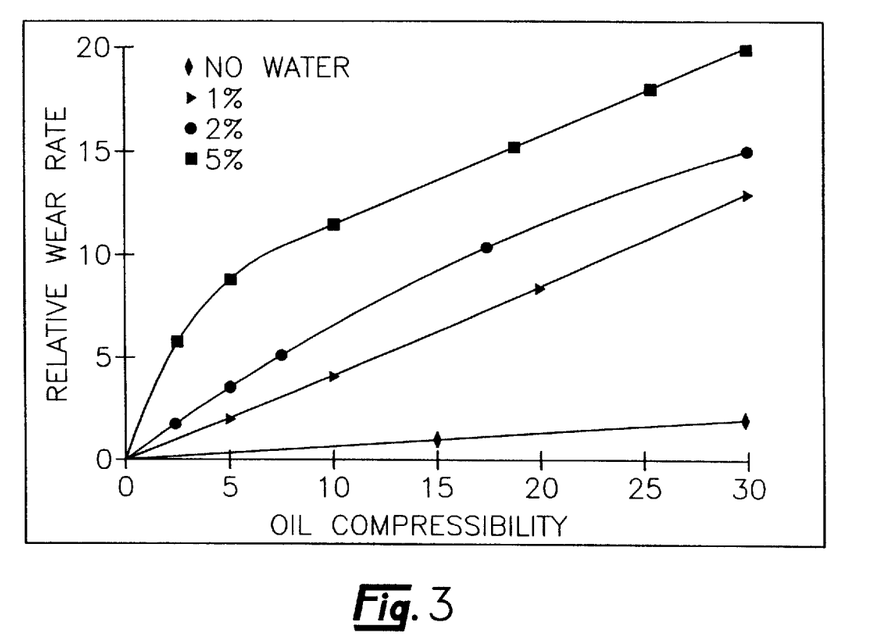
FIG. 3 is a graph of Oil Compressibility vs Relative Wear rate for four levels of entrained water concentration.

This sensitivity of roller elements to moisture contaminated lubrication is illustrated by FIG. 3 which charts a relative wear rate-function along the ordinate against an oil compressibility function along the abscissa for four percentage levels of water entrainment.

Physical units of water contamination measurement are usually given in weight percentages. In appropriate context however, the relative contamination may be stated in volume percentages or even a mixed value of weight per unit of volume.

Wear debris analysis characterizes a diagnostic process for analyzing the products of wear generated by a mechanical system. The objective is to provide information on what wear mechanism is active, which components are wearing, what is the cause of the wear and how long is the remaining useful life of the failing component or system.

Generally, wear debris analysis is a subjective discipline based upon material and shape identity. Material analysis is somewhat quantitative in that an increase in the production of particles of a particular wear element such as iron, copper or aluminum may be quantified by time spaced testing. By distinctive metallurgy or composition, the specific component that produced the wear particles may be identified.

Further insight into the wear process of a system follows a morphological analysis of the wear debris. Examining the size and shape of wear debris is important since wear particles created by abrasion or particle contamination have a different shape than particles produced by load induced adhesive wear or wear caused by other devices such as cavitation.

The foregoing description of lubricating oil tests and the physical units assigned to the test results, have been developed to illustrate the complexity of oil quality analysis. It is an object of the present invention therefore is to simplify the oil analysis process.

Another object of the present invention is to provide a method of objectively combining the myriad of oil test results to resolve a single value, or analog indicative of a machine or system status.

Still another object of the present invention is to provide an apparatus for objectively combining a plurality of directly incomparable test results and finding a single value or analog indicative of a machine or system status.

Yet another object of the present invention is to provide a graphic analog for visual display of a machine or system life or health status.

It is also an object of the invention to organize the various machine life parameters into a composite analog.

SUMMARY OF THE INVENTION

A particular machine or lubrication application is analyzed for a test profile which comprises a battery of tests or analytical procedures having particular relevance to that machine or lubrication application. These are the parameters of the profile. Each test is individually scrutinized to define a potential scope of measured response ranging from test values that are very good for the machine to test values that are very poor or dangerous for the machine. Between these extremes of the defined test value spectrum, a finite number of qualitative increments are defined to provide a total of five, for example, quality increments within the test value spectrum respective to "NORMAL", "HIGH NORMAL", "ALERT", "FAULTY" and "EXTREME". It is not necessary that any of these increments be of equal value range. The only requirement is that a particular test quality increment, "ALERT", for example, is realistically represented by a test value or range of values.

Each test parameter is further categorized as representing one of three evaluation spheres comprising (1) wear, (2) contamination and (3) chemistry. Representatively, large particle rate counts distinguished between ferrous and non-ferrous particles may be a wear sphere parameter. Water, glycol or entrained particle counts are representative contamination parameters. Changes in neutralization values, color index and viscosity are usually chemistry parameters.

Each evaluation sphere is quantatively represented as a vector in a spacial coordinate system. Graphically, three essentially perpendicular vectors are scaled in five units, for example, to correspond with the test parameter quality increments. Each of the vector scale units may also be differentiated by colors.

As an aid in comprehending a complex profile analysis for a lubrication system, all of the test parameters for a given evaluation sphere are reviewed comparatively to select that parameter most negatively advanced. The quality increment value concluded from that most advanced parameter test is assigned to the corresponding evaluation sphere vector.

The foregoing procedure is repeated for the other two vectors and the results plotted to fix three points in space, each point along a vector axis. These three points in space define a triangular resultant plane having a shape and relative area that is representative of and easily comprehended as an analog of the system condition.

When the unit scales of each evaluation vector are representatively connected by respective slabs or planes of color, distinctive color patterns are formed by the resultant planar cut across the laminated color composite. Such color patterns also communicate the system condition.

BRIEF DESCRIPTION OF THE DRAWINGS

The present invention may best be understood by reference to the Description of the Preferred Embodiments and in conjunction with the Drawings wherein.

DESCRIPTION OF THE PREFERRED EMBODIMENTS

For each machine, service or lubrication application, the invention initially requires the definition of a critical parameter profile which is essentially a designation of those lubrication characteristics critical to system life and vitality. Intimately associated with the designation of critical parameter characteristics is a determination of those tests and procedures essential for measuring the respective characteristics.

In a hydraulic power system, for example, it is essential to monitor solid contaminants in the system by particle count. Another critical lubrication characteristic for hydraulic systems is the presence of water in the system. Water may take any or all of three forms in a hydraulic system: (1) nixed or separated as a free compound; (2) emulsified and (3) in dissolved, combination with oil performance additives that were blended with the fresh oil. Relative to the third water form, it is also essential to monitor the depletion of anti-wear additive blended with the fresh oil.

Other monitored characteristics of a hydraulic system parameter profile include the degree of oil oxidation and acidification. Finally, there is a need to monitor the rate of wear to the mechanical components in the system.

For the purpose of system analysis, the numerous measurable lubrication parameters are each assigned to a respective one of three categories corresponding to wear, chemistry and contamination. Lubricant wear is revealed by studying particles and wear metal composition of oil samples. Lubricant chemistry is normally measured by comparing a used oil sample to a reference, looking for changes in the character of the oil base stock or additives. Lubricant contamination analysis measures the amount of water and other foreign fluids in the oil and on counting, sizing and characterizing the entrained solid particles.

Measurable wear parameters may include indices such as the Ferrous and Non-Ferrous Wear indices and the Wear Debris, Analysis, Index of U.S. Pat. No. 5,262,732. Another testing procedure related to the wear parameter category is ferrography, which, by particle analysis, determines the nature, source and extent of a wear mechanism. A spectro metal analysis provides elemental information for iron, chromium, zinc, silicon etc.

The chemistry category of measurable parameters includes values of oxidation, nitration or sulfation degradation derived from Fourier Transform Infrared Spectrometry (FTIR). Wet chemistry is used to determine oil acidity, Total Acid number and Total Base Number. Viscosity is monitored primarily for changes precipitated by certain contaminants or loss of additives. A colormetric or spectral photometric measurement such as described by U.S. Pat. No. 5,194,910 may also be used to indicate chemical changes in the lubricant. The Corrosion Index of U.S. Pat. No. 5,262,732 may be used in the context of this invention as a Chemical Index.

As a category of measurable lubrication parameters, contamination includes parameter values respective to water, glycol, soot, gases, fuel and solids. Values indicative of the relative concentration of such contaminants are measured by FTIR, wet chemistry, gas chromatography, filter patches Karl Fisher processes and the Contamination Index process described by U.S. Pat. No. 5,262,732.

Figure 4:
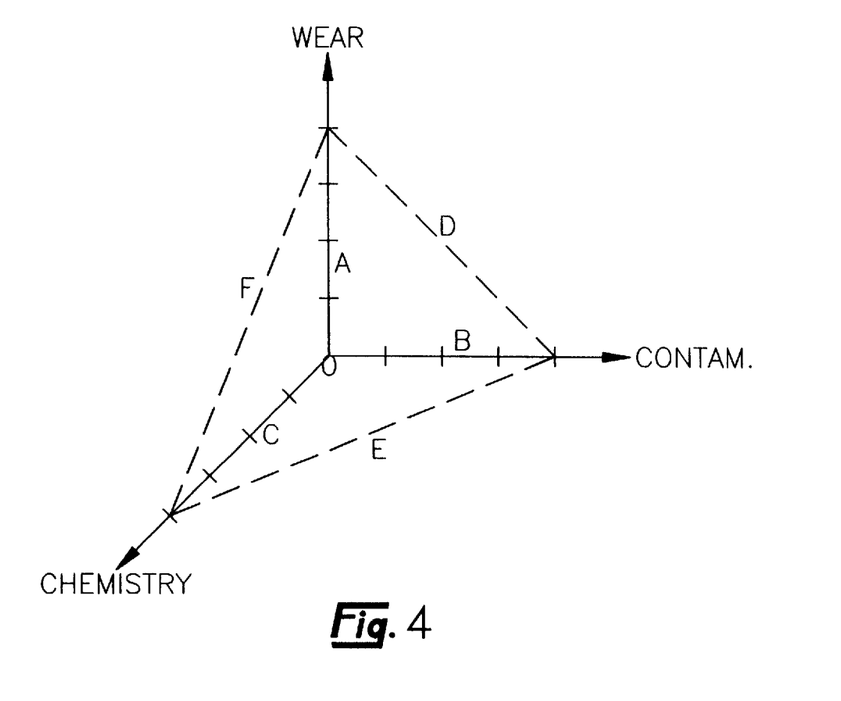
FIG. 4 is a three axis graph of the invention parameter categories.

The invention aligns these three categories of wear, chemistry and contamination as a three dimensional Cartesian coordinate graph with three mutually perpendicular axes as shown by FIG. 4. From the axis origin "0", each axis is segmented into substantially equal increments; five, for example. Superimposition of both direction and quantity lends a vector quality to each of the graph axes. For convenient reference, the WEAR axis is labeled as "A", the CONTAMINATION axis labeled "B" and the CHEMISTRY axis labeled C. A hypotenuse linking the axes "A" and "B" is labeled "D". The hypotenuse linking axes "B" and "C" is labeled "E" and the hypotenuse spanning axes "A" and "C" is labeled "F".

Each of these planar gussets A-B-D, B-C-E and A-C-F linking a pair of axes represents a categorical synergism. For example, wear is greatly accelerated by contamination. Corrosive fluid contamination and abrasive particle contamination lead to rapid wear. There is a similar synergism between system wear and chemistry. The acidity of an oxidized lubricant accelerates the wear process. Depletion of extreme pressure and anti-wear additives can lower the threshold at which mild adhesive wear transitions to severe sliding wear. The synergism between lubricant contamination and lubricant chemistry is illustrated by additive depletion and oil base stock breakdown. These changes lead to an accumulation of contaminating fluids and the formation of sludge. This, in turn, degenerates to inadequate lubrication and high wear rates.

Frequently, all three of these categorical synergies occur simultaneously. Solid contaminants and wear particles cause abrasion producing scratches that are prone to chemical attack. Water and other corrosive fluids combine to generate metal oxide forming chemical reactions that further weaken the load bearing surfaces. Mechanical actions such as stress reversals delaminate the metal oxides thereby causing subsurface cracks to grow, multiply and interconnect. Large spall particles separate from the affected machine element along the interconnected crack lines to add to the solid contaminant accumulation. The process continues until corrections are made or until the machine fails catastrophically.

With the selection of a parameter profile for a specific lubricating system or application, the invention process next requires that a value range be set for each parameter. Subjectively, the value range may, for example, include five quality increments respective to NORMAL, HIGH NORMAL, ALERT, FAULT and EXTREME, for example. Descriptive terms used to differentiate respective quality increments are not critical and are open to considerable creative license. In another example "NORMAL" may correspond with—SAFE—and EXTREME may correspond with—ALARM—.

As applied in the present example, the quality increment characterized as NORMAL is defined as fresh as new. HIGH NORMAL is defined as being of good quality but demonstrating a noticeable change. ALERT is defined as a condition approaching FAULT. FAULT is defined as a status that requires corrective action. EXTREME is defined as beyond corrective action.

Regardless of whether any particular parameter value is unitless, such as a ratio or an index, or expressed in physical units, numbers representing that parameter value also represent the quality of the parameter. Hence a numerical range may be assigned to each increment in the value range of a parameter. Table I catalogs p number of industrially used lubricant evaluation parameters and representative value ranges. Some of the indices of this Table I are the subjects of U.S. Pat. No. 5,262,732 or U.S. patent application Ser. No. 08/578,878 filed Dec. 22, 1995.

TABLE I

| Category | Parameter | Normal High Normal | | Alert Fault | | Extreme |
| --- | --- | --- | --- | --- | --- | --- |
| Wear | Ferrous Index | 3 | 6 | 10 | | 20 |
| | Ferrous Wear Index | 5 | 10 | 15 | | 30 |
| Contamination | Contaminant Index | 4 | 8 | 12 | | 18 |
| Chem or) | ISO 2µ | 19 | 20 | 21 | | 23 |
| Contam) | ISO 5µ | 16 | 17 | 18 | | 20 |
| | ISO 15µ | 13 | 14 | 15 | | 17 |
| | NAS | 8 | 9 | 10 | | 12 |
| | OilLife Index | 4 | 8 | 13 | | 18 |
| (Chem or Contam) | Light Absorbtion Index | 13 | 14 | 15 | | 20 |
| | Chemical | 2 | 4 | 5 | | 7 |

TABLE I-continued

| Category | Parameter | Normal High Normal | | Alert Fault | | Extreme |
| --- | --- | --- | --- | --- | --- | --- |
| | Index | | | | | |
| | % Viscosity Change | 5 | 10 | 15 | | 20 |
| | Color Index | 13 | 14 | 15 | | 20 |
| | Dielectric Index | 8 | 9 | 10 | | 13 |

It will be noted from Table I that some of the listed parameters are designated as classifiable in two parameter categories. In such circumstances, which are not unusual, the parameter value may be tested against a simple discrimination logic predicated on the application, for example, to resolve the conflict. Similar conflicts may arise with respect to two or more parameters in the same parametric category reporting contradictory values. These conflicts are resolved in a similar manner. Specific note should be taken of the fact that the numerical range respective to each quality increment need not be equal to the range of another quality increment for the same parameter. Hence, in some applications, a water content of less than 1% may be considered HIGH NORMAL but a content of greater than 15% considered EXTREME. 2.5% to 7.0% may represent ALERT and 7.1% to 15% may represent FAULT.

From a different perspective, any measured parameter value should be assignable to a proportional or percentage position along a scale having finite limits between NORMAL and EXTREME.

A value range as described is established for each measured parameter respective to a specific sample of lubricant. The measured value of that parameter is assigned a porportional position within the range. From this data body including all parameter values for a given parameter category, that parameter and value that is most advanced toward the EXTREME end of the scale is selected to represent the category on the category axis.

This process is repeated for the two additional categories to place data points proportional to worst case parameter values on each of the parameter category axes. Therefrom, these three data points are linked to define a triangular plane on the three dimensional graph. This triangular plane may be evaluated objectively, as by numerical area values, to provide a single number summation of the system condition.

Figure 5:
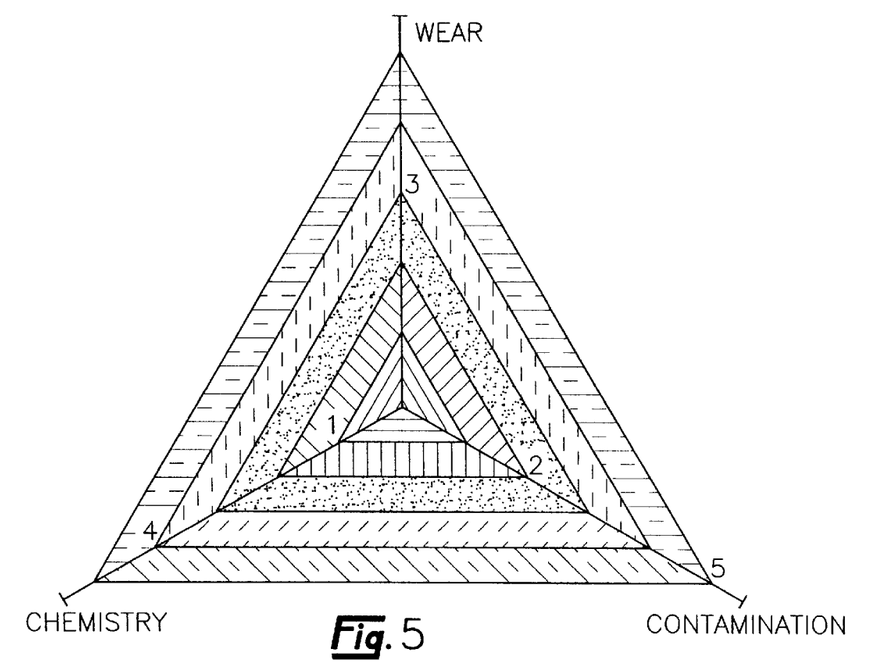
FIG. 5 is a three axis graph of the invention categories with superimposed color increments.

Either alternatively or in addition to an area based conclusion, the three dimensional graph may be color coded as represented by FIG. 5 wherein each of five increments, for example, along the respective parameter category axes are linked by a triangular band of distinctive coloration. As the graph axes are particularized by respective parameter value data points and the three data points linked to form the summation plane, that color outside of the summation plane is removed from the graph to form an instantly percepticle visualization of the system conditon.

Figure 6:
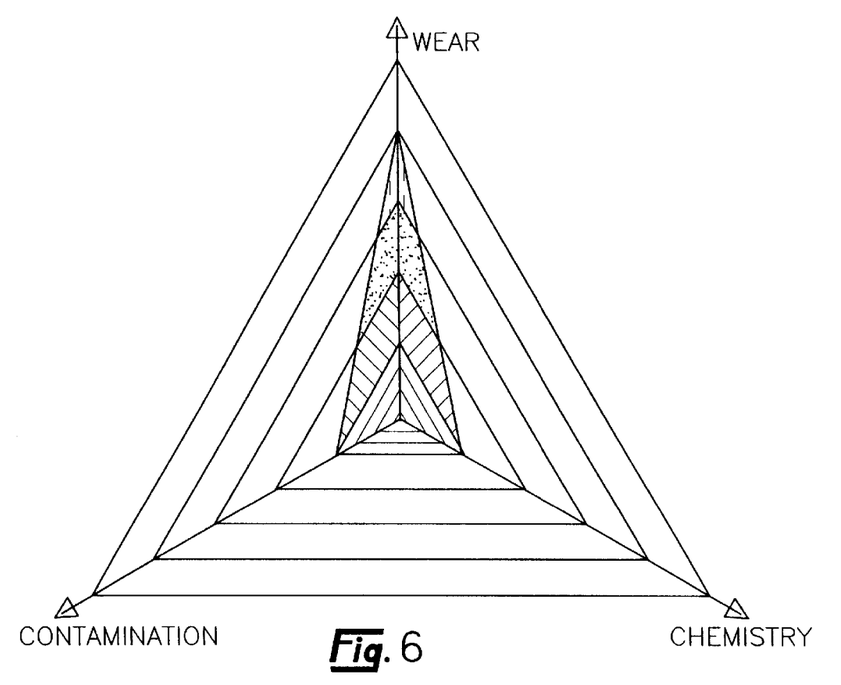
FIGS. 6–9 are three axis graphs of specific applications of the invention.

As a first example of the invention, the lubricant of a gearbox sump respective to a helical speed reducer was analyzed due to the emission of groaning noice from the gear box unit. Analysis parameters selected were the OilLife Index, Ferrous Index, Chemical Index. Contamination Index, % Change in Viscosity, and Ferrous Wear Index. The OilLife Index and Chemical indices all registered 0. The Contamination Index registered 3.2 which, by reference to Table I, is in the NORMAL range increment. However, the Ferrous Index reported 19.0, which by reference to Table I, is very near an EXTREME limit indicating extreme wear on the machine. This Ferrous Index report is supported by a finding of ferrous and non-ferrous particles greater than 60 microns. The graphic report of this analysis is illustrated by FIG. 6 which shows data points on the CONTAMINATION and CHEMISTRY category axes well within acceptable limits but the WEAR category point is approaching an alarm extreme. While this report represents a serious concern for the monitored gearbox, catastropic failure is probably not eminent.

In terms of color translation, assuming the outer or 5 band to be red and the 4 band yellow, no red is showing on this highly elongated summation area. However, the WEAR apex of the triangular area is yellow thereby indicating a measure of concern.

Figure 7:
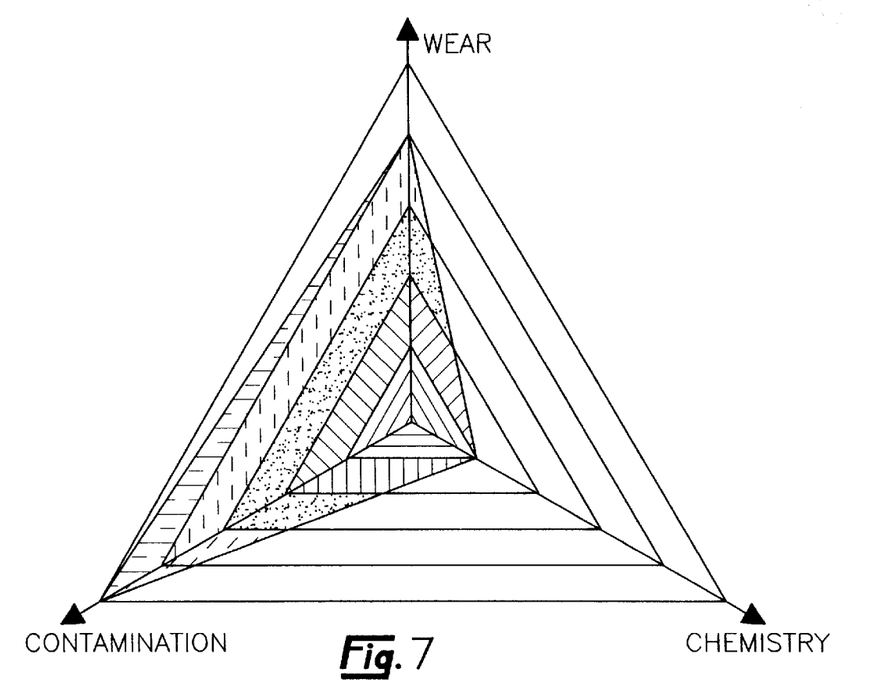

A second example of the invention is an analysis report for the hydraulic fluid used by an industrial production drill press. The CHEMICAL category parameters of OilLife Index and Chemical Index were 0. A Ferrous Index of 16.0 for the WEAR category rates a FAULT value increment. However, a Contamination Index of 256.9 far exceed even the Table EXTREME value of 18. Additionally, the fluid is contaminated with large ferrous and non-ferrous particles. Total water content of the hydraulic fluid was found to be 2.5%. FIG. 7 graphs the analysis conclusion.

Figure 8:
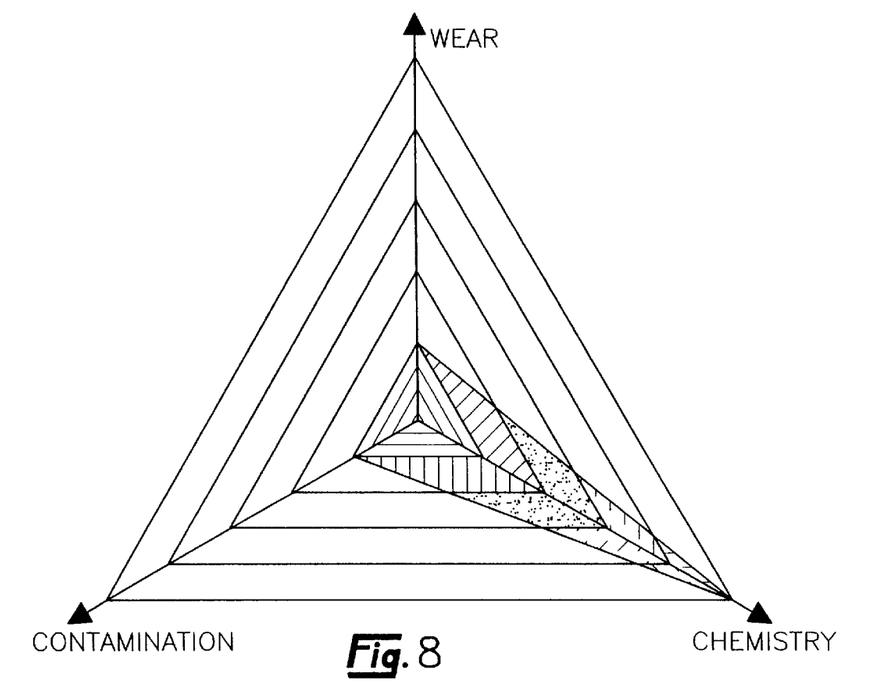

A third example of the invention illustrated by FIG. 8 as reporting the status of final flushing fluid in a new bearing production line, reports an OilLife Index of 36.6, a Chemical Index of 34.6 and a Contamination Index of 0.0. Additionally, the % viscosity change is 85.7. The Ferrous Index is 0.0 and no large contamination particles were found.

Figure 9:
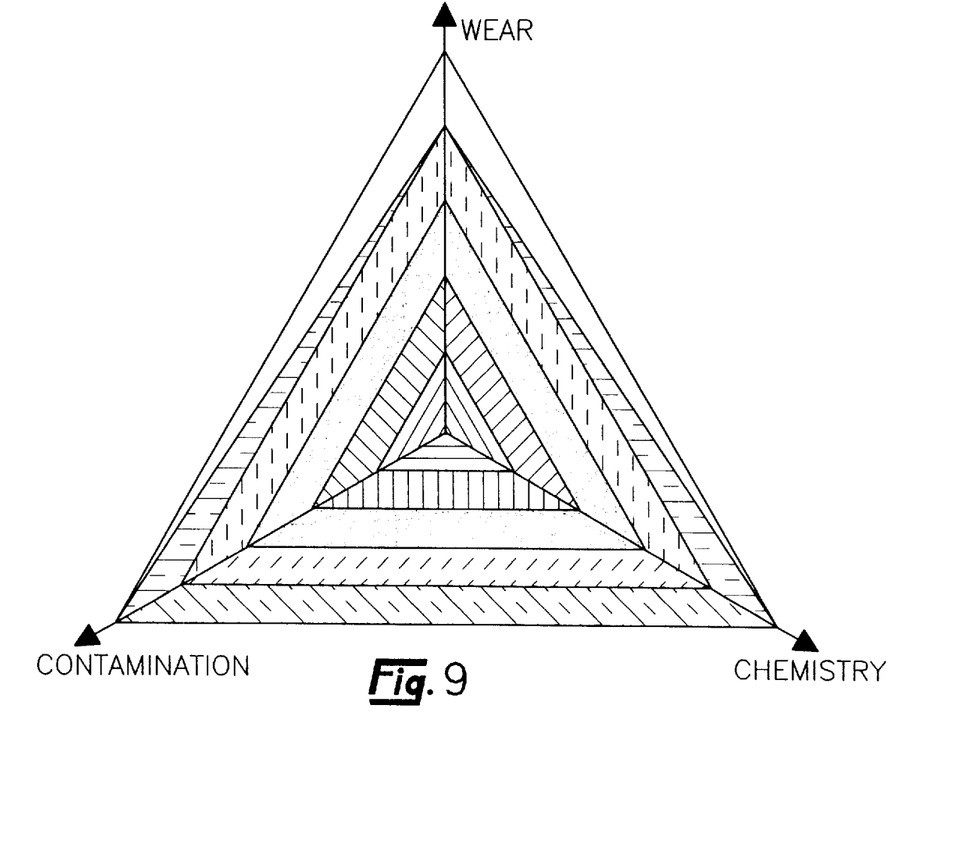

A fourth example of the invention is illustrated by FIG. 9. This graphic summation reports the status of rotary vane pump. The pump lubricant included 14% total water: 89% of that water was free, 1% emulsified and 9% dissolved. The OilLife Index was 759.3. The Chemical Index was 34.3. Both ferrous and non-ferrous large particles were found but the number warranted only a FAULT WEAR condition. In terms of category values, both CONTAMINATION and CHEMISTRY values are EXTREME. Only the WEAR category remains below the EXTREME limit.

Figure 10:
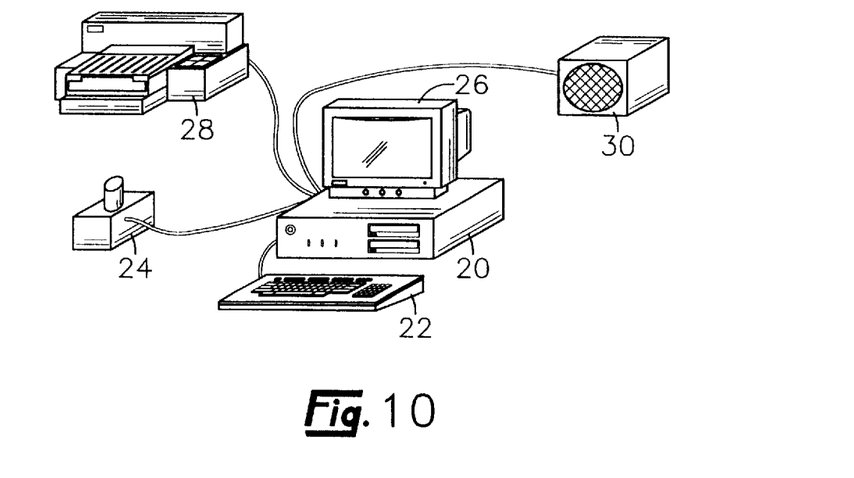
FIG. 10 is a schematic of representative utilities for the invention.

Efficient practice of the invention preferably employs a data processing combination such as is illustrated by FIG. 10. A central data processing unit (CPU) 20 is programmed with data and data processing instructions. These may comprise a tabulation of category segregated parameters for each analysis application proposed for the invention.

A keyboard 22 connected to the CPU 20 provides a manual interface with the data providing program to enter externally acquired data such as ferrographic and wet chemistry values required from a specific sample.

An automatic oil sampling apparatus 24 as described by U.S. Pat. No. 5,262,732 and U.S. patent application Ser. No. 08/578,878 filed Dec. 22, 1995 automatically provides the CPU program with sample data as it is acquired. The video monitor 26 and printer 28 are both media reporting units by which the analysis conclusions are communicated visually to a human manager.

Due to the fact that the areal values of a triangular plane has a direct relationship to the quality state of a monitored system, an audible signal emitted from an audio unit 30 may be employed to generate a sound that is coded to the analysis conclusion.

Having fully described the preferred embodiments of our invention we claim:

1. A method of evaluating the quality status of a lubrication application, said method comprising the steps of:
   defining a specific lubrication application;
   defining a profile of measurable lubrication fluid parameters, each parameter reflecting a quality status of said lubrication application;
   for each of said measurable fluid parameters, defining a spectrum of values between a good parameter quality and an alarming degree of poor parameter quality;
   for each of said fluid parameters, dividing said spectrum of values into a finite number of increments, said number of increments being substantially the same for all fluid parameters;
   defining three parametric categories for said fluid parameters respective to (a) equipment wear, (b) fluid chemistry and (c) fluid contamination;
   assigning each of said fluid parameters to one of said parametric categories;
   defining three, mutually perpendicular, orthogonal axes having said finite number of increments measured from a point of mutual axis origin;
   assigning each of said parametric categories to one of said orthogonal axes;
   from a physical example of said specific lubrication application, measuring said profile parameters;
   respective to the measured parameters of each parametric category, identifying that parameter having a value most advanced toward an alarming degree of poor quality;
   Normalization assigning a data point on each of said orthogonal axes respective to the most advanced parameter value among parameters in the parametric category assigned to each respective axis, said data point being proportionately located within the same increment along the respective axis as was assigned to the respective fluid parameter value; and,
   Linearly connecting the data points respective to each of said axes to define a triangular plane intersecting said axes for an integrated visual display of said three parametric categories, the shape and size of said plane being indicative of the quality status of said physical example of said specific lubrication application.

2. A method as described by claim 1 wherein each increment of a given order of amplitude in parameter value along an axis is connected to other increments of the same order of amplitude in parameter value by a spacial plane of distinctive color.

3. A method as described by claim 1 wherein the parameter profile for the parametric category of contamination comprises an accounting of particles suspended in or circulating with said lubrication fluid.

4. A method as described by claim 3 wherein said accounting comprises a solid particle count.

5. A method as described by claim 4 wherein said solid particle count is of ferrous particles larger than a predetermined minimum.

6. A method as described by claim 4 wherein said solid particle count is of non-ferrous particles larger than a predetermined minimum.

7. A method as described by claim 3 wherein said parametric category of contamination comprises evaluations for the presence of water, glycol, soot, gases or fuel.

8. A method as described by claim 1 wherein said parametric profile for the category of equipment wear comprises a wear particle test.

9. A method as described by claim 1 wherein said parametric profile of fluid chemistry comprises tests for viscosity, color, acidity, oxidation, nitration and sulfation.

10. The combination including at least one instrument for measuring characteristic properties of lubrication fluids used in a mechanical system respective to parametric categories comprising chemistry, contamination and wear, said instruments having a signal transmission connection with a data processing unit for transmitting signals to said data processing unit proportional to measured values of said properties, program control means within said data processing unit for rating each of said measured values with a proportionally positioned point along a respective parameter scale, each parameter scale having a predetermined number of quality increments over a spectrum of quality values between a desirable operating boundary and a highly undesirable operating value, said predetermined number of increments being substantially the same for all of said parameter scales, said program control means further comparing the ratings of substantially all parameter values corresponding to a respective parameter category and isolating that parameter rating most advanced toward undesirable operating qualities to represent the respective parametric category, and visual display means connected with said data processing unit for display of a planar representation of a three dimensional graph having three, mutually perpendicular graph axes, each of said parametric categories being assigned to a respective one of said axes, said program control means including normalization by further placing an axis point along each of the parametric category axes at a location that proportionally corresponds to the proportionally positioned point respective to the isolated parameter representing the parametric category of a respective axis and graphically connecting said axis points with substantially straight lines to form a triangular plane there between that intersects each of said three graph axes for an integrated visual display of said parametric categories.

11. The combination as described by claim 10 wherein said visual display means comprises a video monitor.

12. The combination as described by claim 10 wherein said visual display means comprises a printer.

13. The combination as described by claim 10 further comprising audio alarm means responsive to said program control means.

\* \* \* \* \*

UNITED STATES PATENT AND TRADEMARK OFFICE
CERTIFICATE OF CORRECTION

PATENT NO. : 5,817,928
DATED : October 6, 1998
INVENTOR(S) : Raymond E. Garvey, III et al It is certified that error appears in the above-identified patent and that said Letters Patent is hereby corrected as shown below:

Column 1, line 48, after "metric," delete "less ratios" and insert --unitless ratios--

Column 2, line 23, after "or" delete "dynes)" and insert --(dynes)--

Column 3, line 47, after "Unlike" delete "particle, contamination" and insert --particle contamination,--

Column 3, line 52, after "form" delete "stick" and insert --sticky--

Column 7, Table I, under "Category", delete "Chem or) Contam)" and insert --(Chem or Contam)--

UNITED STATES PATENT AND TRADEMARK OFFICE
CERTIFICATE OF CORRECTION

PATENT NO. : 5,817,928
DATED : October 6, 1998
INVENTOR(S) : Raymond E. Garvey, III, ET AL It is certified that error appears in the above-identified patent and that said Letters Patent is hereby corrected as shown below:

Column 8, line 60, after "groaning" delete "noice" and insert --noise--

In the Claims:

Column 10, Claim 1, line 32 (claim 1) between "Normalization", and "assigning", insert --by--

Column 12, Claim 10, line 12 after "plane" delete "there between" and insert --therebetween--

Signed and Sealed this

Thirtieth Day of March, 1999

Q. TODD DICKINSON

Attest:

Attesting Officer

Acting Commissioner of Patents and Trademarks